United States Patent
Rubio et al.

(10) Patent No.: US 8,394,596 B1
(45) Date of Patent: Mar. 12, 2013

(54) ANTIBODIES AND ASSAYS FOR BETA-N-METHYLAMINO-L-ALANINE

(75) Inventors: Fernando Manuel Rubio, Doylestown, PA (US); Daniel Robert Rubio, Doylestown, PA (US)

(73) Assignee: Abraxis LLC, Warminster, PA (US)

( * ) Notice: Subject to any disclaimer, the term of this patent is extended or adjusted under 35 U.S.C. 154(b) by 0 days.

(21) Appl. No.: 13/585,097

(22) Filed: Aug. 14, 2012

Related U.S. Application Data

(60) Provisional application No. 61/623,659, filed on Apr. 13, 2012.

(51) Int. Cl.
*G01N 33/53* (2006.01)
(52) U.S. Cl. .......................................... 435/7.1; 436/518
(58) Field of Classification Search ........................ None
See application file for complete search history.

(56) References Cited

U.S. PATENT DOCUMENTS

| | | | |
|---|---|---|---|
| 4,762,781 A | 8/1988 | Geffard | |
| 2007/0292893 A1 | 12/2007 | Cox et al. | |
| 2011/0223624 A1 | 9/2011 | Cox | |

FOREIGN PATENT DOCUMENTS

| | | |
|---|---|---|
| WO | WO 00/14538 A1 | 3/2000 |
| WO | WO 01/18059 A2 | 3/2001 |
| WO | WO 2010/014349 A1 | 2/2010 |
| WO | WO 2011/057200 A1 | 5/2011 |

OTHER PUBLICATIONS

Abraxis Package Insert, β-N-methylamino-L-alanine (BMAA) ELISA (Microtiter Plate), Product No. 520040, Apr. 25, 2012.
Carmichael et al., Human Fatalities from Cyanobacteria: Chemical and Biological Evidence for Cyanotoxins, Environ health Perspect., 2001, 109:633-668.
Collings et al., Novel Technologies for the Discovery and Quantitation of Biomarkers of Toxicity, Toxicology, 2008, 245:167-174.
European Application No. 09803340.0, Extended European Search Report dated Aug. 19, 2011.
Huisman, H. et al. (2010), Novel ELISAs for Screening of the Biogenic Amines GABA, Glycine, β-Phenylethylamine, Agmatine, and Taurine Using One Derivatization Procedure of Whole Urine Samples. Anal. Chem. 82 (15): 6526-6533.
Huisman, H. et al. (2009), Studies on the Immune Response and Preparation of Antibodies Against a Large Panel of Conjugated Neurotransmitters and Biogenic Amines: Specific Polyclonal Antibody Response and Tolerance. J. Neurochem., pp. 1-13.
Instruction Manual: DSS and BS3 Crosslinkers, Thermo Fisher Scientific Inc., 2011.
Lawton, L., et al., Chapter 23: Conventional Laboratory Methods for Cyanotoxins, Advances in Experimental Medicine and Biology Springer-Verlag, Berlin, Heidelberger Platz 3, D-14197 Berlin, Germany Series: Advances in Experimantal Medicine and Biology 2008, pp. 513-537 & International Symposium on Cyanobacterial Algal Blooms—State of the Science and Research Needs; Research Triangle Park, NC, USA, Sep. 6-10, 2005.
Meyer, K.H. et al. (1991), Antibodies Against Neuroactive Amino Acids and Neuropeptides. I. A New Two-step Procedure for Their Conjugation to Carrier Proteins and the Production of an Anti-Metenkephalin Antibody Reactive with Gluteraldehyde-fixed Tissues. J. of Histochem. and Cytochem., 39 (6): 749-760.
Skerritt, J.H. et al. (2000), Development of Immunoassays for Tyramine and Tryptamine Toxins of *Phalaris aquatica* L., J. Agric. Food Chem. 48: 27-32.
Thiel et al., Effect on Heterocyst Differentiation of Nitrogen Fixation in Vegetative Cells of the Cyanobacterium *Anabaena variabilis* ATCC 29413, J. Bacteriol., 2001, 183:280-286.
Velthuis et al., In vivo Antinuclear Antibody of the Skin: Diagnostic Significance and Association with Selective Antinuclear Antibodies, Annals of the Rheumatic Diseases, 1990, 49:163-167.

*Primary Examiner* — Jacob Cheu
(74) *Attorney, Agent, or Firm* — Allan H. Fried

(57) ABSTRACT

Antibodies against β-N-methylamino-L-alanine ("BMAA") their production, use and related kits; also the immunogens and methods used to obtain the antibodies.

26 Claims, No Drawings

ANTIBODIES AND ASSAYS FOR BETA-N-METHYLAMINO-L-ALANINE

CROSS REFERENCE TO RELATED APPLICATIONS

This application claims the benefit of U.S. provisional application No. 61/623,659 filed Apr. 13, 2012, which application is incorporated by reference in its entirety herein.

FIELD OF THE INVENTION

The invention relates to the detection of the neurotoxic amino acid, β-N-methylamino-L-alanine (BMAA) by using anti-BMAA antibodies.

BACKGROUND OF THE INVENTION

Prior published work has disclosed the production of anti-BMAA antibodies for the neurotoxic amino acid, BMAA. (US patent application US 2011/0223624, Cox et al.)

The present invention provides a highly sensitive assay for BMAA. Assays for BMAA in the environment are useful to detect BMAA in, for example, sources of drinking water, soil extracts, and the tissues of organisms.

The aims of the invention are met by creating an immunogen that preserves the chemical identity of the ionizable acidic group of BMAA, which in turn allows the production of highly sensitive antibody preparations. As a result, one can detect very low levels of BMAA.

BRIEF SUMMARY OF THE INVENTION

The present invention is a highly sensitive anti-BMAA antibody created according to the following strategy: The BMAA molecule contains three functional moieties: a carboxylate moiety, a secondary amine, and a primary amine. Under physiological conditions, the carboxylate-moiety of BMAA is negatively charged. The present invention creates immunogens in which the carboxylate moiety serves as the immuno-dominant group. Related aspects of the invention include immunoassays and kits for the detection of BMAA.

DETAILED DESCRIPTION OF THE INVENTION

Antibodies of the Invention

In an antibody aspect, the invention is an anti-BMAA antibody preparation capable of detecting BMAA in solution at a concentration within the range of 1 ppb to 300 ppb such that the binding of the antibody preparation to a BMAA conjugate can be reduced in a competition assay by at least 5 percent by BMAA when the BMAA concentration in a solution is within the range of 1 ppb to 300 ppb and the volume of the BMAA solution added to the assay is 50 percent of the final assay volume.

In a particular embodiment of that antibody aspect, the anti-BMAA antibody preparation is capable of detecting BMAA in solution at a concentration within the range of 2.5 ppb to 300 ppb such that the binding of the antibody preparation to a BMAA conjugate can be reduced in a competition assay by at least 5 percent by BMAA when the BMAA concentration in a solution is within the range of 2.5 ppb to 300 ppb and the volume of the BMAA solution added to the assay is 50 percent of the final assay volume.

In a particular embodiment of that antibody aspect, the anti-BMAA antibody preparation is capable of detecting BMAA in solution at a concentration within the range of 2.5 ppb to 100 ppb such that the binding of the antibody preparation to a BMAA conjugate can be reduced in a competition assay by at least 5 percent by BMAA when the BMAA concentration in a solution is within the range of 2.5 ppb to 100 ppb and the volume of the BMAA solution added to the assay is 50 percent of the final assay volume.

In a particular embodiment of that antibody aspect, the anti-BMAA antibody preparation is capable of detecting BMAA in solution at a concentration within the range of 2.5 ppb to 30 ppb such that the binding of the antibody preparation to a BMAA conjugate can be reduced in a competition assay by at least 5 percent by BMAA when the BMAA concentration in a solution is within the range of 2.5 ppb to 30 ppb and the volume of the BMAA solution added to the assay is 50 percent of the final assay volume.

In a particular embodiment of that antibody aspect, the anti-BMAA antibody preparation is capable of detecting BMAA in solution at a concentration within the range of 2.5 ppb to 7.5 ppb such that the binding of the antibody preparation to a BMAA conjugate can be reduced in a competition assay by at least 5 percent by BMAA when the BMAA concentration in a solution is within the range of 2.5 ppb to 7.5 ppb and the volume of the BMAA solution added to the assay is 50 percent of the final assay volume.

Examples are provided herein where 2.5 ppb was detected by an anti-BMAA antibody preparation. It is expected, however, that following the procedures herein will produce anti-BMAA antibody preparations capable of detecting 1.0 ppb.

Whether an antibody preparation qualifies as any one of the foregoing antibody preparations of the invention can be determined by starting with an initial antibody preparation (e.g., undiluted anti-BMAA antiserum) and testing various diluted versions of that initial preparation to determine, for example, whether it can detect BMAA at 2.5 ppb. Typical initial dilutions for testing are in the range 1:000 to 1:25,000 (e.g., 1:1000; 1:3000, 1:8000, and 1:25,000) but other dilutions can be used as needed.

In the antibody aspect, preferred are antibody preparations where the cross reactivity of the preparation with L-cysteine hydrochloride is not more than 1:30; i.e., if the binding of an anti-BMAA antibody preparation to a BMAA conjugate can be reduced, in a competition assay, by 50 percent by a concentration of BMAA denoted as the BMAA-50 concentration, and the binding of the anti-BMAA preparation to the BMAA conjugate is reduced in that same assay (all assay conditions being the same except that L-cysteine hydrochloride is added instead of BMAA) by 50 percent by a concentration of L-cysteine hydrochloride denoted as the CHCl-50 concentration, then the ratio of BMAA-50 to CHCl-50 is the cross reactivity, and is not more than 1:30.

More preferred is where the cross reactivity of the antibody preparation with L-cysteine hydrochloride is not more than 1:100; i.e., if the binding of an anti-BMAA antibody preparation to a BMAA conjugate can be reduced, in a competition assay, by 50 percent by a concentration of BMAA denoted as the BMAA-50 concentration, and the binding of the anti-BMAA preparation to the BMAA conjugate is reduced in that same assay by 50 percent by a concentration of L-cysteine hydrochloride denoted as the CHCl-50 concentration, then the ratio of BMAA-50 to CHCl-50 is the cross reactivity, and is not more than 1:100.

Even more preferred is where the cross reactivity of the antibody preparation with L-cysteine hydrochloride is not more than 1:250; i.e., if the binding of an anti-BMAA antibody preparation to a BMAA conjugate can be reduced, in a competition assay, by 50 percent by a concentration of BMAA denoted as the BMAA-50 concentration, and the binding of the anti-BMAA preparation to the BMAA conjugate is reduced in that same assay by 50 percent by a concentration of L-cysteine hydrochloride denoted as the CHCl-50 concentration, then the ratio of BMAA-50 to CHCl-50 is the cross reactivity, and is not more than 1:250.

Most preferred is where the cross reactivity of the antibody preparation with L-cysteine hydrochloride is not more than 1:500; i.e., if the binding of an anti-BMAA antibody preparation to a BMAA conjugate can be reduced, in a competition assay, by 50 percent by a concentration of BMAA denoted as the BMAA-50 concentration, and the binding of the anti-BMAA preparation to the BMAA conjugate is reduced in that same assay by 50 percent by a concentration of L-cysteine hydrochloride denoted as the CHCl-50 concentration, then the ratio of BMAA-50 to CHCl-50 is the cross reactivity, and is not more than 1:500.

To achieve conditions where the binding of an anti-BMAA antibody preparation to a BMAA conjugate can be reduced, in a competition assay, by 50 percent by a concentration of BMAA, it is preferred that the BMAA concentration be in the range 30 ng/ml to 300 ng/ml most preferably 80 to 200 ng/ml.

Furthermore, the preferred conditions for testing cross-reactivity are summarized as follows: The assay is performed using a solid phase coated with anti-rabbit IgG (the solid phase having been exposed with 7.5 µg/ml anti-rabbit IgG for 12 hours at room temperature, after which well fluid is removed, wells are washed and allowed to dry at room temperature) and 100 µL of either a solution of BMAA of various concentrations (0, 10, 25, 50, 100, 250, 500, 1000 ng/mL) or a solution of L-cysteine hydrochloride at a known concentration (10 ng/mL, 100 ng/mL, 1000 ng/mL, 10 µg/ml, 100 µg/ml, 1000 µg/mL) is added to the wells, 50 µL of a 1:2000 BMAA-HRP solution is added to each well (an initial solution of BMAA-HRP at a concentration of 1 mg/ml is diluted 1:2000), 50 µL of a solution of anti-BMAA antibody solution is added to each well, contents of a well are mixed within the well, and the well contents are incubated for 90 minutes at room temperature (room temperature ° C.), well fluid is removed, wells are washed, 150 µL of a substrate color solution (color solution details: tetramethylbenzidine (TMB), BioFX cat #TMBW-1000 from Surmodics), well contents are mixed, and the well contents are incubated at room temperature (preferably about 25° C.) for 30 minutes, 100 µL of stop solution (2N HCl or sulfuric acid) is added, and the absorbance of the solution is measured at 450 nm.

The foregoing assay (method) characterizes the specificity of the anti-BMAA preparation of the invention as defined by its cross-reactivity with L-cysteine hydrochloride in comparison to its reactivity with BMAA. To utilize the assay for that purpose in the case where the anti-BMAA antibody solution is a diluted antiserum, a 1:8000 dilution of the anti-BMAA antiserum is recommended, especially one isolated according to Example 2 below. However, other dilutions can be used as long as there is a 50 percent binding reduction in the binding of an anti-BMAA antibody preparation to a BMAA conjugate.

The antibody preparation may by monoclonal or polyclonal.

BMAA Conjugates and Immunogens of the Invention

In a conjugate aspect, the invention is a BMAA conjugate (such as an immunogen, also referred to as an immunogenic conjugate), said conjugate comprising BMAA, a salt of BMAA, or a derivative of BMAA, linked to a carrier moiety provided that the BMAA, salt or derivative comprises a free carboxylate moiety.

The "carboxylate" moiety may also be referred to as a "carboxyl" moiety. Moieties may also be referred to as "groups" herein. "Free" means that the carboxlate moiety is not covalently linked to a moiety other than the non-carboxylate portion of BMAA. The carboxylate moiety, —COOH, may or may not be negatively charged as result of the dissociation of the H atom in aqueous solution (a solution comprising water) but for most uses the carboxylate moiety will be negatively charged.

Preferably amide bonds are formed between the carboxyl groups of the carrier molecule and the primary amino group of BMAA. In these circumstances the coupling may, for example, be achieved in a two-step process, by first activating the carboxyl groups on the carrier protein using an activating agent (i.e., the activating agent is the crosslinker), such as 1-ethyl-3-(3-diaminopropyl) carbodiimide hydrochloride (EDC), followed by a nucleophilic reaction with BMAA, or a salt or derivative thereof. Generally the carrier molecule contributes a carboxylic or primary amino group toward formation of the linkage, (e.g., via an active ester or a water soluble carbodiimide.)

Carboxyl groups on the carrier molecule may be activated with EDC for about 2-5 minutes at pH 5, followed by a nucleophilic reaction with BMAA at an alkaline pH in the presence of a molar excess (over EDC) of phosphate. The excess phosphate quenches the EDC, preventing it from activating the carboxylic group of BMAA. The acidic pH is preferably maintained between about 4 and about 6, and the alkaline pH is preferably maintained between about 7.5 and 9.5.

Amino groups (such as lysine residues) of the carrier can also be coupled to the primary amine of the BMAA molecule using homobifunctional reagents such as disuccinimidyl suberate (DSS) or (bis[sulfosuccinimidyl] suberate) ($BS^3$) thereby forming a BMAA-crosslinker derivative. For example, the primary amine group of BMAA was, in the examples below, activated with DSS for 30 minutes using a 2M excess of DSS, followed by a reaction with the lysine residues on the carrier protein at pH 7.0. The reaction pH is preferably maintained between about 6 and 9.

If a BMAA-crosslinker derivative retaining the ionizable acidic group of BMAA, or a salt thereof, is used to create an immunogen to be used to obtain anti-BMAA antibodies, coupling is preferably achieved in a two-step process: (1) carbodiimide-mediated activation of the BMAA under acidic pH conditions with a molar excess of phosphate, and (2) reacting the activated carboxylic group of the BMAA with the amino groups of the carrier molecule under alkaline pH conditions. The acidic pH is preferably maintained between about 4 and 6, and the alkaline pH is preferably maintained between about 7.5 and 9.5.

Derivatives of BMAA can also be coupled to carrier proteins using DSS or $BS^3$.

Non-limiting examples of carrier molecules useful in preparation of the immunogen invention include porcine thyroglobulin, bovine serum albumin, human serum albumin, ovalbumin, and keyhole limpet hemocyanin. Preferred are proteins, such as porcine thyroglobulin (TG) or bovine serum albumin (BSA). The preferred molecular weight range for the carrier molecule is from about 10,000 to about 10,000,000 (daltons).

The immunogen is used with host animals using conventional techniques to raise antibodies.

The preparation of monoclonal antibodies is disclosed, for example, by Kohler and Milstein, *Nature* 256:495-7, 1975; and Harlow et al., in: *Antibodies: a Laboratory Manual*, Cold Spring Harbor Pub., 1988). Monoclonal antibodies may be obtained by injecting mice, or other small mammals, with a composition comprising the immunogenic conjugate, confirming the presence of anti-BMAA antibodies in the serum, removing the spleen to obtain B lymphocytes, fusing the B lymphocytes with myeloma cells to produce hybridomas, cloning the hybridomas, selecting positive clones that produce antibodies to BMAA, and isolating the antibodies from the hybridoma cultures. The monoclonal antibodies can be purified from hybridoma cultures by a variety of well-established techniques, non-limiting examples being affinity chromatography with Protein-A Sepharose, size-exclusion chromatography, and ion-exchange chromatography. See, for example, Baines et al., Purification of Immunoglobulin G (IgG), in: *Methods in Mol. Biol., .LQ:.* 79-104, 1992). Antibodies may also be derived from subhuman primate antibodies. Methods for raising antibodies in baboons can be found, for example, in Goldenberg et al., International Patent Publication WO 91/11465 (1991) and Losman et al., *Int. J. Cancer,* 4:310-314, 1990.

The term "antibody" as used in this invention refers to not only intact molecules but also as functional fragments thereof, such as Fab, F(ab')$_2$, and Fv that are capable of binding BMAA, or a salt thereof, especially after the BMAA or salt thereof has been derivatized with a linker molecule as disclosed herein. These functional antibody fragments are defined as follows:

(1) Fab, a fragment which contains a monovalent antigen-binding fragment of the antibody, obtainable by digestion of the antibody with papain to yield an intact light chain and a portion of one heavy chain;

(2) Fab', a fragment of an antibody obtainable by treating the antibody with pepsin, followed by reduction, to yield an intact light chain and a portion of the heavy chain, two Fab' fragments are obtained per antibody molecule;

(3) Fab')$_2$, a fragment of an antibody, it can be obtained by treating the antibody with pepsin without subsequent reduction; F(ab')$_2$ is a dimer of two Fab' fragments held together by two disulfide bonds;

(4) Fv, is a genetically engineered fragment containing the variable region of the light chain and the variable region of the heavy chain expressed as two chains; and (5) A single chain antibody ("SCA"), a genetically engineered molecule containing the variable region of the light chain and the variable region of the heavy chain, linked by a polypeptide.

Methods of making these fragments are known in the art. (See for example, Harlow and Lane, *Antibodies: A Laboratory Manual*, Cold Spring Harbor Laboratory, New York, 1988).

Antibody fragments can be prepared by proteolytic hydrolysis of the antibody, such as by pepsin or papain digestion, or by expression in *E. coli* of DNA encoding the fragment. Enzymatic cleavage with pepsin can create a 5S fragment denoted as F(ab')$_2$. This fragment can be further cleaved using a thiol reducing agent (optionally using a blocking group for the sulfhydryl groups resulting from cleavage of disulfide linkages) to produce 3.5S Fab' monovalent fragments. Also, enzymatic cleavage with pepsin can create two monovalent Fab' fragments and an Fc fragment directly. See, for example U.S. Pat. Nos. 4,036,945 and 4,331,647, and references contained therein, which patents are hereby incorporated by reference in their entirety. See also Porter, R. R., *Biochem. J., Z*: 119-126, 1959. Other cleavage methods may also be used. What is essential is that the fragments bind to the antigen that is recognized by the intact antibody.

Fv fragments comprise an association of VH and VL chains. This association may be noncovalent, as described in Inbar et al., *Proc. Nat'l Acad. Sci. USA* 0:2659-62, 1972. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. In recombinant host cells, a single polypeptide chain with a linker peptide bridging the two V domains will be produced. Methods for producing sFvs are described, for example, by Whitlow and Filpula, *Methods,* 2: 97-105, 1991; Bird et al., *Science* 242:423-426, 1988; Pack et al., *Bio/Technology* X1:1271-77, 1993; and Ladner et al. U.S. Pat. No. 4,946,778, which is hereby incorporated by reference in its entirety.

An antibody fragment can be a peptide comprising a single complementarity-determining region (CDR) can be obtained by constructing genes encoding the CDR. Such genes can be prepared by using the polymerase chain reaction with the variable region of RNA of antibody-producing cells. See, for example, Larrick and Fry, Methods, 2: 106-10, 1991.

Process for Making an Immunogenic Conjugate, Label Conjugate or a Coating Conjugate In a conjugation process aspect, the invention is also a process for making a conjugate using a cross-linker moiety, the process comprising the steps of:

a) Covalently linking an amine moiety on a BMAA moiety, a salt of BMAA or a derivative of BMAA to a crosslinker moiety; and b) Covalently linking a protein to said crosslinker moiety; wherein step (a) may precede step (b), occur simultaneously with step (b) or occur after step (b), provided that the result of steps (a) and (b) results in said BMAA, salt or derivative comprising a free carboxylate moiety.

In a first embodiment of the conjugation process aspect, the invention is a process for making a conjugate using a cross-linker moiety (also referred to as an "activating agent"), the process comprising the steps of:

a) Covalently linking an amine moiety on a BMAA moiety, a salt of BMAA or a derivative of BMAA to a crosslinker moiety to obtain a BMAA-crosslinker moiety; and b) Covalently linking a protein to said BMAA-crosslinker moiety;

In that first embodiment, the crosslinker moiety is selected from the group consisting of DSS and BS$^3$.

In a second embodiment of the conjugation process aspect, the invention is a process for making a conjugate using a cross-linker moiety the process comprising the steps of:

a) Covalently linking a protein to a crosslinker moiety to obtain a protein-crosslinker moiety; and b) Covalently linking an amine moiety on a BMAA moiety, a salt of BMAA or a derivative of BMAA to the protein-crosslinker moiety.

In an example of that second conjugation aspect of the process, the amine moiety is the primary amine moiety of BMAA and the crosslinker moiety is EDC.

In another example of that second conjugation aspect of the process, the carboxyl moiety of the protein and the primary amine moiety of BMAA are coupled in a two-step process comprising the steps of:

a) reacting the carboxyl groups on the carrier protein with the cross linker moiety to form a protein-crosslinker moiety, and b) initiating a nucleophilic reaction with BMAA, or a salt or derivative thereof, to covalently link the BMAA to the protein-crosslinker moiety under alkaline pH in the presence of a molar excess of phosphate.

The primary amine moiety of BMAA may be activated using the cross-linker moiety 1-ethyl-3-(3-diaminopropyl) carbodiimide hydrochloride (EDC).

A preferred use of the conjugate is as an immunogen to make BMAA. Another preferred use is as a coating conjugates in invention ELISA-based assays for detection of BMAA. The conjugate may be labeled ("labeled conjugate"), that is either directly or indirectly detectable. An example of indirect detection is where the label is an enzyme such as HRP that catalyzes a chemical reaction that can be monitored colorimetrically.

It is preferred that if one such conjugate is an immunogenic conjugate (one used as an immunogen to make antibodies for an immunoassay for BMAA), then the coating conjugate to be used in that immunoassay will have been made using a different protein than for the immunogenic conjugate. For example, if thyroglobulin was the carrier protein in the immunogenic conjugate(s) used to obtain anti-BMAA antibody(ies) for an immunoassay, then the carrier protein in coating conjugate used for that immunoassay should not be thyroglobulin, but rather be selected from, for example, bovine serum albumin or ovalbumin. However, the coating conjugate should mimic the ionic characteristics of the immunogenic conjugate to the extent that a negatively charged group in the BMAA, a derivative containing BMAA's ionizable acidic group, or salt(s) thereof, is preserved. It is preferred, but not necessary, that a BMAA derivative used to make the coating conjugate be identical to the BMAA derivative used to make the immunogenic conjugate.

Immunoassays of the Invention

In an immunoassay aspect, the invention is a process comprising the following steps:

a) Contacting a test sample with an anti-BMAA antibody of the invention; and
b) Measuring the amount of material in the test sample that binds to the anti-BMAA antibody.

Preferably, the assay comprises a step where an antibody-BMAA complex is linked to a solid support.

In a first more specific the immunoassay aspect, the invention may (this is the process followed in the Examples below) comprise the following steps:

a) coating a solid support (e.g., a well), with a secondary antibody (such as anti-rabbit IgG) said secondary antibody capable of binding to an anti-BMAA antibody of the invention;
b) contacting a fluid test sample (e.g., an aliquot of lake water considered to possibly contain BMAA) with the secondary antibody on the solid support;
c) adding a detectable BMAA conjugate with the fluid test sample;
d) adding, as a primary antibody, an anti-BMAA antibody of the invention to the fluid test sample, such that the primary antibody will bind to the secondary antibody and thereby be secured to the solid support, and further such that BMAA in the fluid test sample can compete with the detectable BMAA conjugate for binding to the anti-BMAA antibody,
e) removing, from contact with the solid support, the portion of the fluid test sample not bound to the anti-BMAA antibody; and
f) measuring the amount of detectable BMAA conjugate bound to anti-BMAA antibodies bound to the secondary antibodies bound to the solid support. The greater the amount of BMAA in the test sample, the smaller the amount of detectable BMAA conjugate that will be detected by the measurement.

In a particular embodiment of the first more specific immunoassay aspect, the detectable BMAA conjugate is an enzyme conjugate. In that embodiment, after step (e) and prior to step (f), the immunoassay further comprises adding a substrate for the enzyme component of the conjugate.

In a second more specific immunoassay aspect, the invention is a process comprising the following steps:

(a) contacting a test sample with an anti-BMAA antibody of the invention;
(b) contacting the test sample with a solid phase coated with a coating conjugate comprising a carrier molecule covalently coupled to BMAA, a derivative thereof or a salt thereof (such that only anti-BMAA antibody unreacted with BMAA in the test sample will be free to react with the BMAA moiety of the coating conjugate);
(c) removing unbound components from the solid phase, and
(d) detecting the presence of bound anti-BMAA antibody. The amount of bound antibody is inversely related to the amount of the BMAA, its derivative, or salt, in the test sample.

In a particular embodiment of the second more specific immunoassay aspect, the anti-BMAA antibody is covalently linked to an enzyme. In that embodiment, after step (c) and prior to step (d), the immunoassay further comprises adding a substrate for the enzyme linked to the antibody.

Preferably, the anti-BMAA antibody is contacted with the test sample at a pH of about 5 to 9.

The immunoassays may be implemented, for example, with BMAA attached to a detectable label (e.g., to HRP via across-linker) or an anti-BMAA antibody attached to a detectable label. For example, anti-BMAA antibody may be conjugated to biotin which can be detected with an enzyme-labeled molecule that binds to the biotin. It can also be implemented by binding to the anti-BMAA antibody on the solid phase to a secondary antibody, where the secondary antibody is conjugated to a signal-generating agent, for example, an enzyme, radioisotope, chemiluminescent or fluorescent label, colored microbead, colloidal gold, or other signal-generating agent.

In preferred embodiments, the assay also comprises performing a control assay. The control assay is done in identical fashion as the immunoassay except, instead of a test sample, a sample with a known amount of BMAA is tested. More preferably more than one sample with a known amount of BMAA is tested.

Examples of signal-generating agents are signal-generating radioisotopes, signal-generating chromogenic agents, signal-generating fluorogenic agents, and signal-generating catalytic agents.

Signal-generating radioisotopes include, for example, tritium, carbon 14, phosphorous 32, iodine 125, and iodine 131, can be attached to an antibody by methods known in the art. See, for example, H. Uan Vunakis and J. J. Langone, Editors, *Methods in Enzymology*, Vol. 70, Part A, 1980.

Signal-generating chromogenic agents include, for example, compounds that absorb visible or UV light. Examples are dyes such as quinoline, triarylmethane, phthalein, azo, anthraquinoid, cyanine, and phenazoxonium dyes.

Signal-generating fluorogenic agents include, for example, those that emit visible or UV light subsequent to irradiation by light. Fluorogens can also be used with quencher molecules. See, for example, J. J. Langone, H. Van Vunakis et al., *Methods in Enzymology*, Vol. 74, Part C, 1981; also U.S. Pat.

No. 4,366,241; also U.S. Pat. No. 3,996,345, which patents are incorporated by reference herein.

Signal-generating catalytic agents include, for example, alkaline phosphatase, horseradish peroxidase, luciferase, (3-galactosidase, glucose oxidase, lysozyme, malate dehydrogenase, and glucose-6-phosphate dehydrogenase. Dual catalytic systems include alkaline phosphatase—glucose oxidase using glucose-6-phosphate, also the oxidation of glucose to hydrogen peroxide by glucose oxidase, followed by use of a leuco dye. See for example, U.S. Pat. No. 4,366,241 and, U.S. Pat. No. 4,740,468, which are incorporated herein by reference.

Reagents for coupling enzymes to antibodies are well known and include, for example, glutaraldehyde, p-toluene diisocyanate, carbodiimide reagents, p-benzoquinone, m-periodate, and N,N'-ophenylenedimaleimide. (see, for example, J. H. Kennedy et al., *Clin. Chim Acta* 2$Q$:1 (1976)). Preferred agents are, for example, horseradish peroxidase and alkaline phosphatase.

Signal-generating chemiluminescent labels can be used. See, for example, U.S. Pat. No. 4,104,029, incorporated by reference herein.

The substrates for catalytic systems include, for example, chromogens and fluorogens such as pars-nitrophenyl phosphate (PNPP), P-D-glucose (optionally with a redox dye), homovanillic acid, o-dianisidine, bromocresol purple powder, 4-alkyl-umbelliferone, luminol, pars-dimethylaminoiophine, and paramethoxylophine.

The term "solid phase" are supports used in immunoassays. They are insoluble in water. Example include but are not limited to filter paper, the wells of plastic microtiter plates, glass membranes, plastic beads, test tubes, strips, and magnetic particles.

Fluid can be removed from test wells, etc. by methods well known in the art: pouring, pipetting, aspiration, etc. Removal is preferably followed by washing to remove residues of the original fluid.

The assays can be done at any temperature where it detects BMAA. However, room temperature is preferred. The temperatures for the determination will preferably range from about 10° C. to about 37° C., preferably from about 15° C. to about 25° C.

Kits of the Invention

A kit of the invention comprises:
a) an anti-BMAA antibody of the invention; and
b) a signal generating agent; where the signal-generating agent is optionally linked to another moiety (for example, the signal generating agent may be HRP that is linked to BMAA).

In some embodiments, the kit further comprises a solid phase to which the antibody can be bound (either directly or indirectly).

In a preferred embodiment, the signal generating agent is linked to—or is a part of—a conjugate of BMAA. In another preferred embodiment, the signal generating agent is attached to the anti-BMAA antibody.

The kit preferably comprises written information either indicating how to use the kit for detecting BMAA or indicating how to obtain information on how to use the kit for detecting BMAA.

Invention test kit(s) may comprise reagents for use in assaying BMAA. For example, the enzyme substrate if the signal generating agent is an enzyme, buffer solutions for carrying out the reactions, and wash solutions. They preferably contain vials (or other containers) with known amounts of BMAA, which can be used to calibrate the assay performed using the kits.

Invention test kit(s) are useful for determining the concentration of BMAA or salt(s) thereof contained in such test samples taken from a variety of sources, e.g., a drinking water supply, an extract of an environmental specimen, an extract of a plant or soil specimen, an extract of a biological specimen, and the like. The detection sensitivity for BMAA in the immunoassay is discussed above. The sensitivity can be about 0.1 ppb if the SPE procedures set forth are followed.

The invention is described below in greater detail by reference to the following non-limiting Examples. All chemicals used in these Examples were reagent grade and commercially available from sources such as Sigma (St. Louis, Mo.), Molecular Devices (Sunnyvale, Calif.), Corning (Kennebunck, Mass.), or Surmodics/BioFx (Eden Prairie, Minn.).

Example 1

Preparation of TG-EDC-BMAA, BSA-EDC-BMAA, and HRP-EDC-BMAA Via Glutamic Acid and Aspartic Acid Residues (For additional background on this procedure see PCT publication WO 00/14538)

Conjugates of BMAA with BSA or with HRP were prepared by activating, in the absence of BMAA, the carboxylic groups of BSA or HRP with EDC thereby forming BSA-EDC or HRP-EDC. This was followed by the coupling of the activated carboxylate groups on the carrier protein to the primary amino group of BMAA. The procedure was as follows: 50 mg of EDC and 5 mg of sulfo-NHS (Sulfo-N-hydroxysuccinimide) were added to 15 mg of BSA or HRP pre-dissolved in 5 ml of 10 mM $KH_2PO_4$, pH 5.0. The reaction mixture was stirred for 2-3 minutes, thereby forming BSA-EDC or HRP-EDC, followed by the addition of 5 mL of a 1% solution of BMAA in 0.2 M $K_2HPO_4$, pH 8.5. After the solution was stirred overnight, the conjugate (BSA-EDC-BMAA or HRP-EDC-BMAA) was dialyzed exhaustively against PBS-7.4 (0.14 M NaCl, 10 mM $K_2HPO_4$, pH 7.4) or TBS-8 (tris-buffered saline, pH 8). Conjugates were stored at $\leq$20° C. (20° C. or less) By this procedure the conjugate was formed by linkage of BMAA to the carrier protein predominantly via the glutamic and aspartic acid residues of the carrier protein.

TG-EDC-BMAA conjugates can be prepared by the same procedure.

Example 2

Preparation of TG-DSS-BMAA, HRP-DSS-BMAA and BSA-DSS-BMAA Via Lysine Residues (For additional background on this procedure see J. Agric. Food Chem. vol. 48, pages 27-32, 2000)

Conjugates of BMAA with HRP or with BSA were prepared by activating the primary amine group of BMAA followed by coupling to the primary amino group on carrier lysine residues using DSS under conditions that kept the ionizable carboxyl group of BMAA free. 10 mg BMAA in 1.0 mL of deionized water was added to 20 mg of DSS dissolved in 1.0 mL of dry DMSO. The reaction mixture was stirred 30 minutes at room temperature (even 2 minutes of stirring might be enough), thereby forming BMAA-DSS. 10 mg of HRP or BSA in 2 mL of 10 mM phosphate buffer pH 7.0 was then added. After the solution was stirred for 2 hours, the conjugate (HRP-DSS-BMAA or BSA-DSS-BMAA) was dialyzed exhaustively against PBS-7.4 (0.14 M NaCl, 10 mM $K_2HPO_4$, pH 7.4) or TBS-8 (tris-buffered saline, pH 8). Both conjugates were stored at ≦20° C. By this procedure the conjugate was formed by linkage of BMAA to the carrier protein predominantly via the lysine residues on the carrier protein.

TG-DSS-BMAA conjugates can be prepared by the same procedure.

Example 3

Production of Antibodies

Antibodies to BSA-BMAA conjugate were produced in New Zealand white rabbits as follows:

Rabbits were immunized with 0.5-1.0 mg of immunizing conjugate per rabbit per injection. The immunizing conjugate was emulsified with Complete Freund's Adjuvant for primary injections and with Incomplete Freund's Adjuvant for booster injections. Three or four booster injections were performed at monthly intervals to raise the desired titers. The rabbits were bled on 12±3 days following each booster injection. Antisera were monitored for titer and analyte specificity by capturing the relevant antibodies on ELISA plates coated with anti-rabbit IgG. The captured antibodies were measured in a subsequent step by incubating the plates with a BMAA-horseradish peroxidase (BMAA-HRP).

Three rabbits were immunized with an immunogen in which EDC was used to link BMAA to BSA according to Example 1. Three rabbits were immunized with an immunogen in which DSS was used to link BMAA to BSA according to Example 2. The rabbit with the highest antibody titer when tested with sera collected 14 days after the fourth booster was a rabbit that had been immunized with an immunogen in which DSS was used to link BMAA to BSA according to Example 2. Antibodies from that rabbit, harvested 14 days after the fourth booster were used to generate the data obtained from Example 6 below. Antibodies from that rabbit, harvested 14 days after the fourth booster were used to generate the data obtained from Example 8 below. A rabbits immunized with an immunogen in which EDC was used to link BMAA to BSA according to Example 1 also displayed a useful antibody titer but not as high as the rabbit with the highest titer referred to above.

Example 4

Preparation of HRP-BMAA (DSS)

Conjugates of HRP were prepared by activating the primary amine group of BMAA followed by their coupling to the primary amino group on HRP using DSS. 10 mg BMAA in 1.0 mL of deionized water was added to 20 mg of DSS dissolved in 1.0 mL of dry DMSO. The reaction mixture was stirred 30 minutes at room temperature (even 2 minutes of stirring might be enough). 5 mg of HRP in 2 mL of 10 mM phosphate buffer pH 7.0 was then added. After the solution was stirred for 2 hours, the conjugate (HRP-BMAA) was dialyzed exhaustively against PBS-7.4 (0.14 M NaCl, 10 mM $K_2HPO_4$, pH 7.4) or TBS-8 (tris-buffered saline, pH 8). Conjugate was diluted 1:1 with glycerol and stored at −20° C.

Example 5

ELISA for BMAA Using Antibody-Coated Plates

The ELISA method:
1. Add either 100 μL of either a BMAA solution (0, 10, 25, 50, 100, 250, 500, 1000 ng/mL of BMAA) as a calibrator/standard solutions or 100 μL of a test sample into the wells of the test strips (coated with anti-rabbit IgG). Analysis in duplicate or triplicate is recommended.
2. Add 50 μL of enzyme conjugate solution (BMAA-HRP) to the individual wells successively using a multi-channel pipette or a stepping pipette.
3. Add 50 μL of antibody solution (rabbit anti-BMAA; for example one made by diluting by a factor of 8000 antiserum from a rabbit immunized according to Example 3 using BMAA-BSA as the immunogen) to the individual wells successively using a multi-channel pipette or a stepping pipette. Cover the wells with parafilm or tape and mix the contents by moving the strip holder in a circular motion on the benchtop for 30 seconds. Be careful not to spill the contents. The foregoing creates a total assay volume of 200 μL.
4. Incubate the strips for 90 minutes at room temperature.
5. Remove the covering and decant the contents of the wells into a sink. Wash the strips four times using the diluted washing buffer solution (1×PBS with 0.1% Tween), using at least a volume of 250 μL of washing buffer for each well in each washing step. Remaining buffer in the wells should be removed by patting the inverted plate dry on a stack of paper towels.
6. Add 150 μL of substrate (color) solution ((TMB), BioFX cat #TMBW-1000 from Surmodics), to the wells. Cover the wells with parafilm or tape and mix the contents by moving the strip holder in a circular motion on the benchtop for 30 seconds. Be careful not to spill the contents. Incubate the strips for 30 minutes at room temperature. Protect the strips from direct sunlight.
7. Add 100 μL of stop solution (2N HCl) to the wells in the same sequence as for the substrate solution.
8. Read the absorbance at 450 nm using a microplate ELISA photometer within 15 minutes after the addition of stopping solution using a computer interfaced ELISA reader (Molecular Devices, Sunnyvale, Calif.). BMAA concentration in the unknown samples was estimated by comparison with a concurrently-run standard curve.

Example 6

Estimate of Sensitivity

The procedure of Example 5 was followed using known amounts of BMAA. The results are shown in Table 1. (The antibody preparation was that specified in Example 3 as having been used for Example 6). "Concentration (ng/ml)" refers to the concentration of the BMAA in the 100 μL of calibrator/standard solution referred to in step (1) of Example 5.

The sensitivity of the assay is the concentration of BMAA needed to reduce B/Bo by 5 percent compared to its value when no BMAA is in the calibrator/standard solution. The sensitivity was calculated to be 7.5 ppb.

TABLE 1

| Concentration (ng/ml) | B/Bo (%) |
| --- | --- |
| 10 | 93 |
| 25 | 85 |
| 50 | 77 |
| 100 | 64 |
| 250 | 44 |
| 500 | 29 |
| 1000 | 18 |

Example 7

Cross Reactivity of the Anti-BMAA Antibody with Other Compounds

The procedure of Example 6 was followed with various other compounds except that in some cases, the highest concentration tested was either more than or less than the highest concentration tested in Example 6 (1 μg/ml). For D,L-2,4-Diamiobutyric acid hydrochloride, the highest concentration tested was 1,000 μg/ml. For Microscystin-LR and Cylindrospermopsin, the highest concentration tested was 0.1 μg/ml.

The "cross-reactivity", is the concentration of the compound that was required to provide the same signal as that corresponding to 50% inhibition in the assay as caused by BMAA at 170 nanograms/ml. ("170 nanograms/ml" refers to the concentration of the BMAA in the standard curve obtained by adding 100 μL of standard solution referred to in step (1) of Example 5.) If 500 times as much of a compound is required (i.e., 85,000 ng/ml=85 μg/ml or 85 micrograms/ml), then the cross reactivity is specified as the percent equivalent of 1/500; i.e., 0.2%.

Consistent with Example 5, the other compounds were not tested at concentrations greater than 1 μg/ml. If a 5% decrease in signal was not observed when testing compounds at 1 μg/ml or less, then the cross-reactivity is listed as "None up to 1 μg/ml". Some other compounds were not tested at concentrations greater than 0.1 μg/ml. If a 5% decrease in signal was not observed when testing compounds at 0.1 μg/ml or less, then the cross-reactivity is listed as "None up to 0.1 μg/ml". Compounds exhibiting 0.2% cross-reactivity were tested at concentrations up to 500 ug/mL, those exhibiting 0.1% cross-reactivity were tested at concentrations up to 1 mg/ml.

The results are shown in Table 2.

TABLE 2

| Compound(s) | Cross-reactivity |
|---|---|
| B β-N-methylamino-L-alanine (BMAA) | 100% |
| L-Cysteine hydrochloride; L-Glutamic acid; L-Aspartic acid; γ-Aminobutyric acid | 0.2% |
| D,L-2,4-Diaminobutyric acid hydrochloride | 0.1% |
| Glycine; L-isoleucine; L-Lysine monohydrochloride; L-Histidine monohydrochloride monohydrate; L-Tryptophan; L-alanine; L-Tyrosine; L-Valine; L-Cystine; L-Asparagine; L-Phenylalanine; L-Threonine; L-Proline;; L-Arginine monohydrochloride; L-Glutamine, L-Methionine; trans-4-hydroxy-L-proline; L-Serine; L-Leucine | None up to 1 μg/ml |
| Microcystin-LR; Cylindrospermopsin | None up to 0.1 μg/ml |

Example 8

Second Estimate of Sensitivity

The procedure of Example 6 was followed except that (1) the BMAA concentrations tested were 5, 10, 25, 100, 250 and 500 ppb (corresponding to 5, 10, 25, 100, 250 and 500 ng/ml) and (2) an antibody preparation harvested later than that used for Example 6 was used. The antibodies harvested for this example were harvested after the 6$^{th}$ boost.

The results are shown in Table 3. The sensitivity of the assay was estimated to be 2.5 ppb.

TABLE 3

| Concentration (ng/ml) | B/Bo (%) |
|---|---|
| 5 | 93 |
| 10 | 88 |
| 25 | 77 |
| 100 | 49 |
| 250 | 30 |
| 500 | 19 |

Example 9

Testing of Lake Water Samples

The ability of the assay to determine the amount of BMAA in lake water was tested by adding ("spiking") BMAA to water samples from five lakes that, in the absence of the added BMAA did not have detectable amounts of BMAA. The testing was done using the procedure of Example 5 with the antibody preparation (sensitivity=2.5 ppb) used for Example 8. In each case, the BMAA concentration in the sample was determined to be less than 5 ppb. When 50 ppb of BMAA was added, the measured amounts of BMAA in the samples were, according to the assay: 49.6 ppb, 53.1 ppb, 45.7 ppb, 53.6 ppb, and 47.1 ppb respectively.

Example 10

BMAA Solid Phase Extraction Procedure

Solid phase extraction (SPE) for matrix cleanup or for concentration of samples was tested for its ability to concentrate BMAA in a water sample, in this case, distilled water. Prior to the start of the SPE procedure, A 10 ml BMAA sample was created by adding BMAA to a concentration of 0.25 ppb. The procedure used was as follows:

Solvents:
 Equilibration solution: 100% Methanol
 Conditioning solution: 100 mM Formic Acid
  Prepared by adding 1.695 mL Reagent-Grade Formic Acid (>95%, Sigma #F0507) to 400 mL de-ionized water
 Formate washing solution: 2% (v/v) Formic Acid
  Prepared by adding 8.0 mL Reagent-Grade Formic Acid (>95%, Sigma #F0507) to 392 mL de-ionized water
 Methanol washing solution: 100% Methanol
 Eluting Solution: 5% (v/v) Ammonium hydroxide in (1:1) Methanol:Acetonitrile
  Prepared by adding 2.0 mL ammonium hydroxide (EM Science #AX1303-6) to 40 mL MeOH:ACN Sample Preparation:
 The sample (10 mL) was acidified to facilitate SPE adsorption. The sample was acidified with concentrated HCl to a final concentration of 0.01 M hydrochloric acid.

SPE Column:
 Phenomenex Strata-X-C 33u (200 mg/3 mL) in vacuum manifold @ flow-rate 0.5-1.0 mL/min Concentration Procedure:
1. Equilibrated the Strata-X-C SPE using 3 mL of 100% methanol
2. Conditioned the Strata-X-C SPE using two-passes of 3 mL 100 mM formic acid
3. Passed 10 mL "acidified" sample through column—BMAA will be retained on SPE column
4. Washed with 3 mL 2% formic acid
5. Washed with 3 mL 100% methanol 6. Eluted retained BMAA with three-passes of 1 mL 5% ammonium hydroxide in (1:1) methanol:acetonitrile
7. Evaporated eluted sample under nitrogen gas
8. Reconstituted dried BMAA with 1.0 mL de-ionized water
9. Adjusted pH of reconstituted sample to neutral pH using sodium hydroxide
10. The eluates were saved for BMAA analysis by ELISA (Example 5)

Use of the above procedure resulted in increasing the concentration of the BMAA in the sample, initially at 0.25 ppb, to a detectable level: 2.5 ppb using the antibody that, as described in Example 8, had a sensitivity of 2.5 ppb.

It follows that, if the procedure is proportionally scaled up for use with a 25 mL sample, it is expected that a sample initially at a BMAA concentration of 0.1 ppb can be concentrated to a detectable concentration of 2.5 ppb.

While the invention has been described in detail with reference to certain preferred embodiments thereof, it will be understood that modifications and variations are within the spirit and scope of that which is described and claimed.

What is claimed is:

1. An anti β-N-methylamino-L-alanine (anti-BMAA) antibody preparation capable of detecting BMAA in solution at a concentration within the range of 1 ppb to 300 ppb such that the binding of the antibody preparation to a BMAA conjugate can be reduced in a competition assay by at least 5 percent by BMAA when the BMAA concentration in a solution is within the range of 1 ppb to 300 ppb and the volume of the BMAA solution added to the assay is 50 percent of the final assay volume.

2. An anti-BMAA antibody preparation of claim 1 wherein the antibody preparation is capable of detecting BMAA in solution at a concentration within the range of 2.5 ppb to 300 ppb such that the binding of the antibody preparation to a BMAA conjugate can be reduced in a competition assay by at least 5 percent by BMAA when the BMAA concentration in a solution is within the range of 2.5 ppb to 300 ppb and the volume of the BMAA solution added to the assay is 50 percent of the final assay volume.

3. An anti-BMAA antibody preparation of claim 2 wherein the preparation is capable of detecting BMAA in solution at a concentration within the range of 2.5 ppb to 100 ppb such that the binding of the antibody preparation to a BMAA conjugate can be reduced in a competition assay by at least 5 percent by BMAA when the BMAA concentration in a solution is within the range of 2.5 ppb to 100 ppb and the volume of the BMAA solution added to the assay is 50 percent of the final assay volume.

4. An anti-BMAA antibody preparation of claim 3 wherein the preparation is capable of detecting BMAA in solution at a concentration within the range of 2.5 ppb to 30 ppb such that the binding of the antibody preparation to a BMAA conjugate can be reduced in a competition assay by at least 5 percent by BMAA when the BMAA concentration in a solution is within the range of 2.5 ppb to 30 ppb and the volume of the BMAA solution added to the assay is 50 percent of the final assay volume.

5. An anti-BMAA antibody preparation of claim 4 wherein the preparation is capable of detecting BMAA in solution at a concentration within the range of 2.5 ppb to 7.5 ppb such that the binding of the antibody preparation to a BMAA conjugate can be reduced in a competition assay by at least 5 percent by BMAA when the BMAA concentration in a solution is within the range of 2.5 ppb to 7.5 ppb and the volume of the BMAA solution added to the assay is 50 percent of the final assay volume.

6. An anti-BMAA antibody preparation of claim 1 wherein the cross reactivity of the antibody preparation with L-cysteine hydrochloride is not more than 1:30.

7. An anti-BMAA antibody preparation of claim 1 wherein the cross reactivity of the antibody preparation with L-cysteine hydrochloride is not more than 1:100.

8. An anti-BMAA antibody preparation of claim 1 wherein the cross reactivity of the antibody preparation with L-cysteine hydrochloride is not more than 1:250.

9. An anti-BMAA antibody preparation of claim 2 wherein the cross reactivity of the antibody preparation with L-cysteine hydrochloride is not more than 1:30.

10. An anti-BMAA antibody preparation of claim 2 wherein the cross reactivity of the antibody preparation with L-cysteine hydrochloride is not more than 1:100.

11. An anti-BMAA antibody preparation of claim 2 wherein the cross reactivity of the antibody preparation with L-cysteine hydrochloride is not more than 1:250.

12. An anti-BMAA antibody preparation of claim 3 wherein the cross reactivity of the antibody preparation with L-cysteine hydrochloride is not more than 1:30.

13. An anti-BMAA antibody preparation of claim 3 wherein the cross reactivity of the antibody preparation with L-cysteine hydrochloride is not more than 1:100.

14. An anti-BMAA antibody preparation of claim 3 wherein the cross reactivity of the antibody preparation with L-cysteine hydrochloride is not more than 1:250.

15. An anti-BMAA antibody preparation of claim 4 wherein the cross reactivity of the antibody preparation with L-cysteine hydrochloride is not more than 1:30.

16. An anti-BMAA antibody preparation of claim 4 wherein the cross reactivity of the antibody preparation with L-cysteine hydrochloride is not more than 1:100.

17. An anti-BMAA antibody preparation of claim 4 wherein the cross reactivity of the antibody preparation with L-cysteine hydrochloride is not more than 1:250.

18. An anti-BMAA antibody preparation of claim 5 wherein the cross reactivity of the antibody preparation with L-cysteine hydrochloride is not more than 1:30.

19. An anti-BMAA antibody preparation of claim 5 wherein the cross reactivity of the antibody preparation with L-cysteine hydrochloride is not more than 1:100.

20. An anti-BMAA antibody preparation of claim 5 wherein the cross reactivity of the antibody preparation with L-cysteine hydrochloride is not more than 1:250.

21. A kit for the detection of BMAA, said kit comprising:
a. an anti-BMAA antibody preparation of claim 1; and
b. a signal generating agent.

22. A kit of claim 21, said kit comprising written information either indicating how to use the kit for detecting BMAA or indicating how to obtain information on how to use the kit for detecting BMAA.

23. A kit for the detection of BMAA, said kit comprising:
a. an anti-BMAA antibody preparation of claim 2; and
b. a signal generating agent.

24. A kit of claim 23, said kit comprising written information either indicating how to use the kit for detecting BMAA or indicating how to obtain information on how to use the kit for detecting BMAA.

25. A kit for the detection of BMAA, said kit comprising:
a. an anti-BMAA antibody preparation of claim 7; and
b. a signal generating agent.

26. A kit of claim 25, said kit comprising written information either indicating how to use the kit for detecting BMAA or indicating how to obtain information on how to use the kit for detecting BMAA.

* * * * *